(12) United States Patent
Tsubouchi et al.

(10) Patent No.: US 10,888,419 B2
(45) Date of Patent: Jan. 12, 2021

(54) CONTINUOUSLY ADJUSTABLE CUTTING TOOL FOR PREPARING VALVE LEAFLET

(71) Applicant: TERUMO CARDIOVASCULAR SYSTEMS CORPORATION, Ann Arbor, MI (US)

(72) Inventors: Takeshi Tsubouchi, Dexter, MI (US); Randal J. Kadykowski, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 103 days.

(21) Appl. No.: 16/227,315

(22) Filed: Dec. 20, 2018

(65) Prior Publication Data

US 2019/0125526 A1  May 2, 2019

Related U.S. Application Data

(63) Continuation of application No. PCT/US2017/052151, filed on Sep. 19, 2017.

(60) Provisional application No. 62/396,919, filed on Sep. 20, 2016.

(51) Int. Cl.
 *A61F 2/24* (2006.01)
 *A61B 17/3205* (2006.01)
 *A61B 17/32* (2006.01)

(52) U.S. Cl.
 CPC ...... *A61F 2/2415* (2013.01); *A61B 17/32053* (2013.01); *A61F 2/24* (2013.01); *A61B 2017/320052* (2013.01)

(58) Field of Classification Search
 CPC ... A61B 17/32053; A61B 2017/320052; A61F 2/2415; A61F 2/24
 USPC .......................................................... 600/36
 See application file for complete search history.

(56) References Cited

U.S. PATENT DOCUMENTS

| | | | |
|---|---|---|---|
| 1,864,489 A | 6/1932 | Gennrich | |
| 5,609,600 A * | 3/1997 | Love ...................... | A61B 17/32 606/167 |
| 5,716,399 A | 2/1998 | Love | |
| 5,885,228 A | 3/1999 | Rosenman et al. | |
| 6,491,511 B1 * | 12/2002 | Duran ................... | A61F 2/2415 425/394 |
| 6,497,713 B1 | 12/2002 | Tompkins et al. | |
| 9,414,920 B2 * | 8/2016 | Ozaki ................... | A61F 2/2415 |
| 2002/0091441 A1 * | 7/2002 | Guzik ................... | A61F 2/2457 623/2.13 |
| 2006/0229716 A1 * | 10/2006 | Mitrev ................. | A61B 5/1072 623/2.11 |

(Continued)

*Primary Examiner* — Navin Natnithithadha
*Assistant Examiner* — Sunita Reddy
(74) *Attorney, Agent, or Firm* — Darryl Newell; MacMillan, Sobanski & Todd LLC (57) ABSTRACT

A device prepares leaflets for cardiovascular valve reconstruction from a pericardial tissue sheet harvested from a patient. A cutting tool is adapted to cut a predetermined pattern having a selected leaflet size. The device is continuously adjustable using a plurality of slidable blade segments forming a closed periphery. Radially-slidable links are slidably attached to respective blade segments. An adjustment disc is coupled to the links, wherein rotation of the adjustment disc varies a radial position of the links to modify an overlapping of the blade segments in order to select a corresponding size of the closed periphery.

6 Claims, 13 Drawing Sheets

(56) References Cited

U.S. PATENT DOCUMENTS

| | | | |
|---|---|---|---|
| 2007/0251364 A1* | 11/2007 | Blumle | B26F 1/384 83/100 |
| 2009/0149775 A1 | 6/2009 | Lander | |
| 2010/0018447 A1* | 1/2010 | Holecek | A61F 2/2415 112/217.1 |
| 2011/0251598 A1* | 10/2011 | Ozaki | A61F 2/2415 606/1 |
| 2012/0035720 A1* | 2/2012 | Cali | A61F 2/2415 623/2.16 |
| 2013/0013058 A1* | 1/2013 | Umezu | A61F 2/2415 623/2.12 |
| 2013/0089655 A1* | 4/2013 | Gregg | A61F 2/2415 427/2.25 |
| 2016/0221206 A1* | 8/2016 | Jeske | B31B 50/20 |

\* cited by examiner

CONTINUOUSLY ADJUSTABLE CUTTING TOOL FOR PREPARING VALVE LEAFLET

CROSS REFERENCE TO RELATED APPLICATIONS

This application is a continuation of PCT Application No. PCT/US2017/052151, filed Sep. 19, 2017, based on and claiming priority to U.S. Provisional Application No. 62/396,919, filed Sep. 20, 2016, both of which are incorporated herein by reference in their entirety.

STATEMENT REGARDING FEDERALLY SPONSORED RESEARCH

Not Applicable.

BACKGROUND OF THE INVENTION

The present invention relates in general to cutting a heart valve leaflet from a pericardium membrane for use in valve repair/reconstruction, and, more specifically, to devices and systems for cutting a valve leaflet according to various desired sizes with a single, adjustable device.

One type of heart surgery relates to heart valve repair or replacement. For a patient with a damaged valve leaflet (e.g., in a bicuspid or tricuspid valve), there is a surgical technique for repairing the valve leaflet using the patient's own pericardium tissue, bovine tissue, or a synthetic material. A manmade synthetic valve has good durability but requires continuous use of an anti-coagulate drug. A valve leaflet reconstruction operation using pericardium tissue removed from the patient is becoming a preferred technique. A thin sheet of pericardium tissue harvested from the patient must be cut and shaped according to the required size of the replaced leaflet. The cut leaflet is then sewn into the original position of the diseased leaflet. This therapy appears to have longer viability compared to a bovine tissue valve, and it is generally safe from rejection since this therapy uses the patient's own tissue.

More specifically, the procedure for valve leaflet repair may include the following steps. Circulatory support incisions are made and a perfusion system (i.e., heart lung machine) is connected. The target heart valve (e.g., aortic valve) is then exposed. A thin sheet of pericardium tissue is excised and prepared by treatment with known chemicals. The damaged valve leaflet is trimmed away. A sizing tool is used in order to measure the site (e.g., valve width) to which the new leaflet will be attached. The processed pericardium tissue is placed on a backing plate. Using a template corresponding to the measured size and a marking pen, the desired size and shape for a replacement leaflet is stenciled onto the tissue sheet. The locations (e.g. up to 15 dots) for forming individual sutures may also be marked. Using scissors, the stenciled leaflet is manually cut and trimmed from the tissue sheet. The leaflet is sutured onto the valve annulus and the leaflet commissures are sutured.

During the time that the cut and trim tasks are performed, the heart is stopped and the patient is supported by external circulation using oxygenator and blood pump. This has unfavorable effects on the body, so the duration needs to be minimized. Thus, it would be desirable to minimize valve leaflet preparation time while obtaining more accurately shaped leaflets, thereby contributing to better outcomes of the therapy.

SUMMARY OF THE INVENTION

In one aspect of the invention, a device is provided for preparing leaflets for cardiovascular valve reconstruction, comprising a plurality of slidable blade segments forming a closed periphery. Radially-slidable links are slidably attached to respective blade segments. An adjustment disc is coupled to the links, wherein rotation of the adjustment disc varies a radial position of the links to modify an overlapping of the blade segments in order to select a corresponding size of the closed periphery.

DETAILED DESCRIPTION OF PREFERRED EMBODIMENTS

Figure 1:
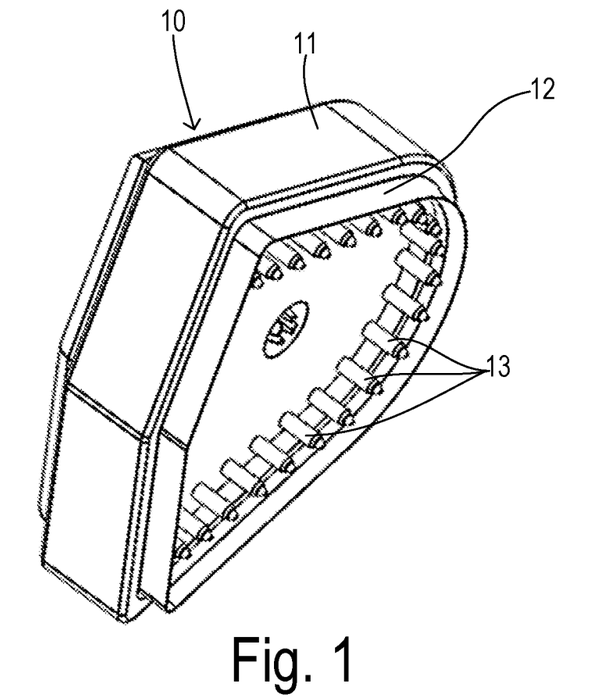
FIG. 1 is a perspective view of a cutting/marking device for obtaining a leaflet from a membrane sheet.
Figure 2:
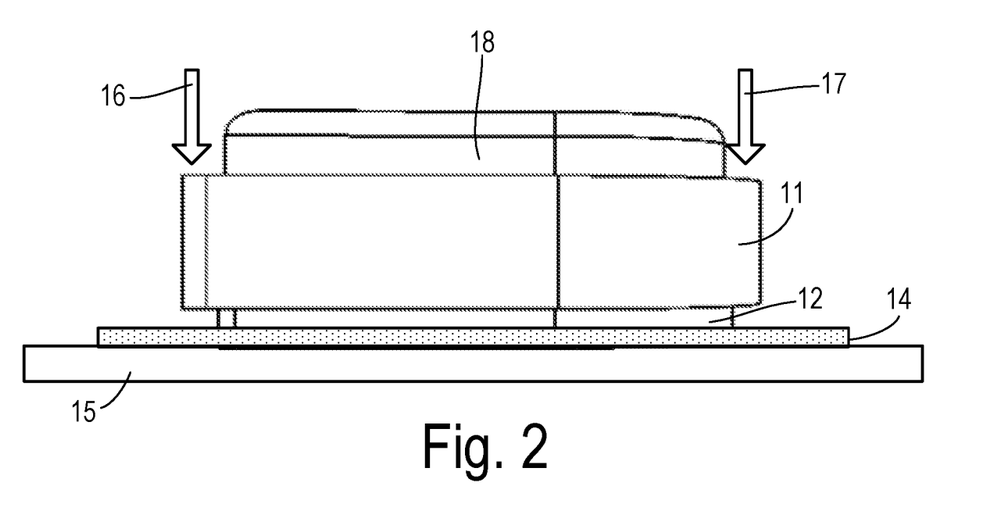
FIG. 2 is a side view of the device of FIG. 1 being used to cut a leaflet.
Figure 3:
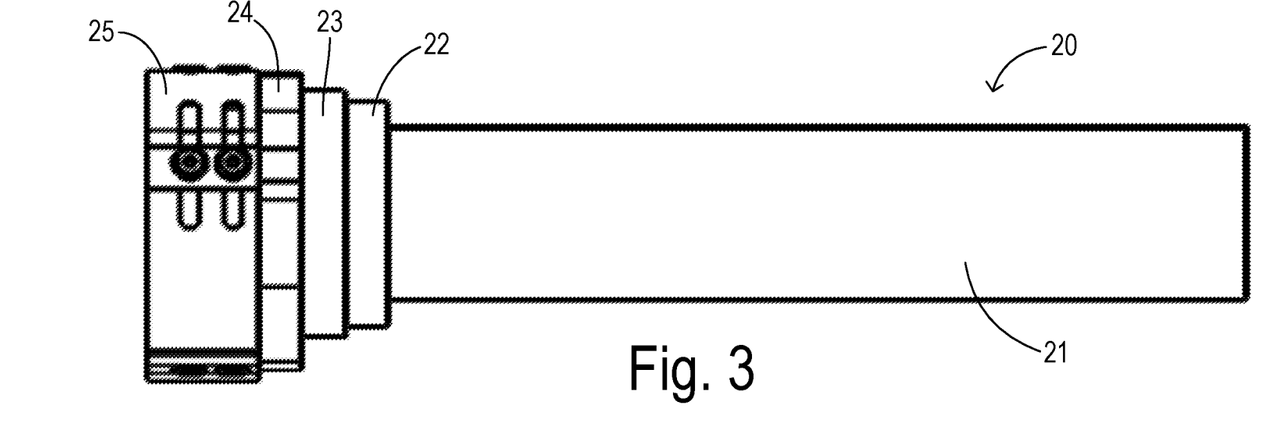
FIG. 3 is a side view of an adjustable cutting tool according to one embodiment of the invention.
Figure 4:
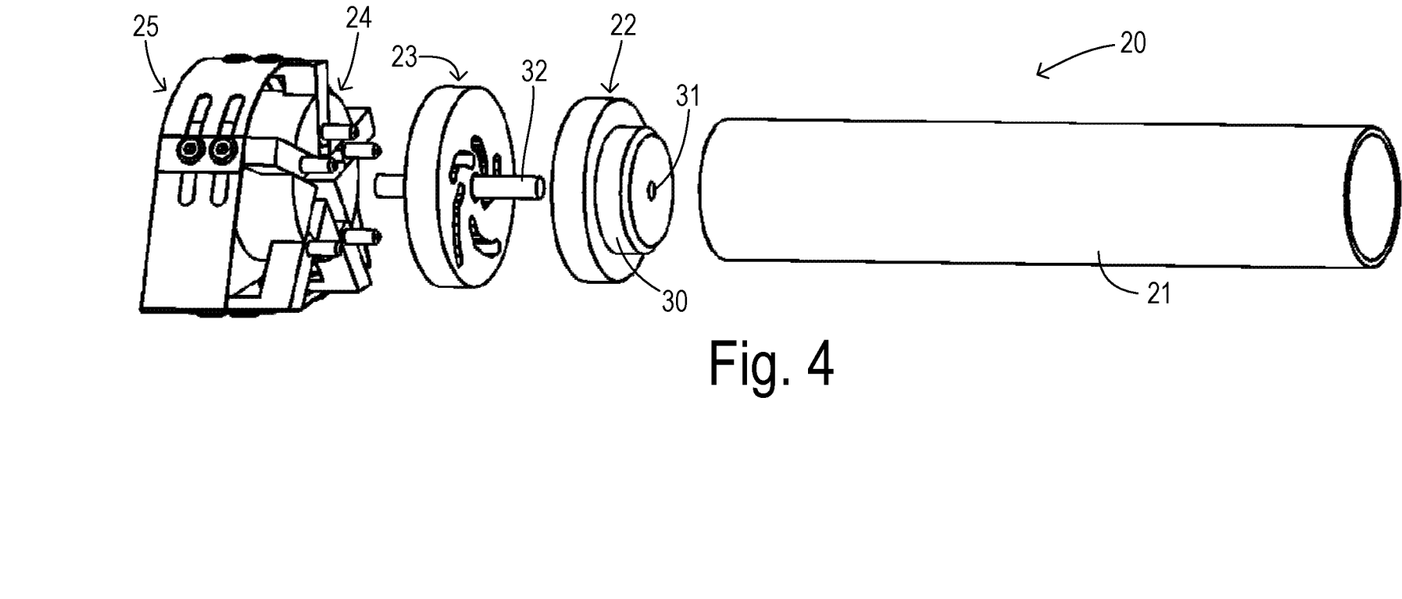
FIG. 4 is an partially exploded view of the tool of FIG. 3.
Figure 5:
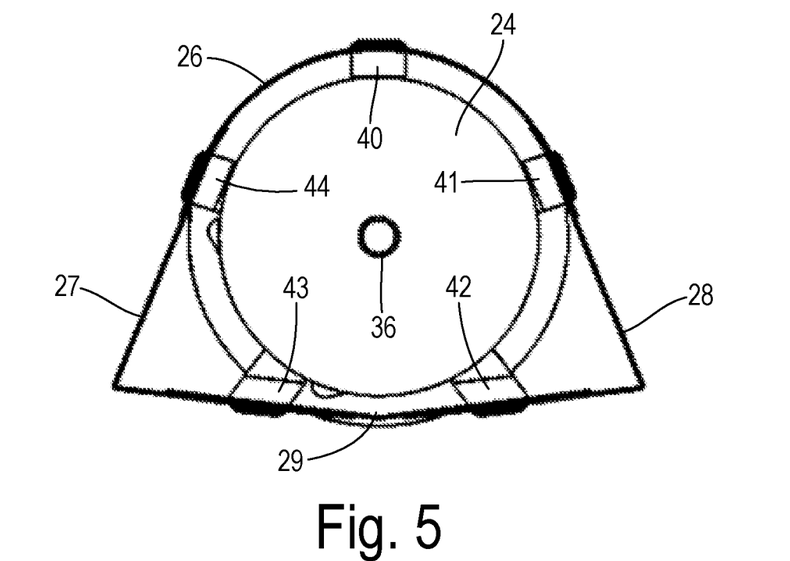
FIG. 5 is an end view of the tool of FIG. 3.

A "cookie cutter" type of leaflet cutting and marking device 10 is shown in FIGS. 1 and 2. A main body 11 supports a cutting blade 12 on a bottom side. Preferably, main body 11 generally conforms to and is slightly larger than a desired leaflet profile. Cutting blade 12 provides a cutting edge following a precisely configured cutting pattern according to a selected leaflet dimension. The particular size for which device 10 is configured may preferably be labeled on the device so that a kit having a plurality of differently sized cutting devices can be bundled to support a surgical procedure. A plurality of ink applicators 13 extend from main body 11 at positions inset from blade 12. In order to cut a desired leaflet, a pericardial membrane 14 is placed on a hard backing surface (e.g., metal plate) 15. Main body 11 is pressed downward with a downward force shown at 16 and 17 so that cutting blade 12 penetrates membrane 14 in one quick motion.

In order to provide a correct leaflet size, a surgeon measures a patient's aortic structures. A plurality of devices 10 each having a different respective leaflet size can be maintained so that the device having a size most closely matching the measured size can be selected when cutting the membrane sheet.

In order to avoid the need for maintaining a collection of cutting tools with different leaflet sizes, an adjustable cutting tool 20 is provided as shown in FIGS. 3-18. In a first embodiment, a "cookie-cutter" type of tool 20 having an adjustable size for cutting a leaflet matching a desired size has a tubular handle 21 receiving a base 22, an adjustment wheel 23, and a cam block 24. Cam block 24 supports a continuous blade cutting blade 25 comprised of slidable segments 26, 27, 28, and 29.

Base 22 has a shank 30 for mounting within handle 21, e.g., by interference fit or bonding. A bore 31 through base 22 receives one end of a shaft 32. Shaft 32 remains fixed within bore 31 by an interference fit or bonding so that shaft 32 does not rotate relative to handle 21. Adjustment wheel 23 has a center bore 35 which loosely receives shaft 32 so that wheel 23 is rotatable with respect to handle 21. A second end of shaft 32 is received in a bore 36 within cam block 24 in a non-movable, non-rotatable manner. Thus, cam block 24 is likewise fixed against rotation with respect to handle 21.

Figure 6:
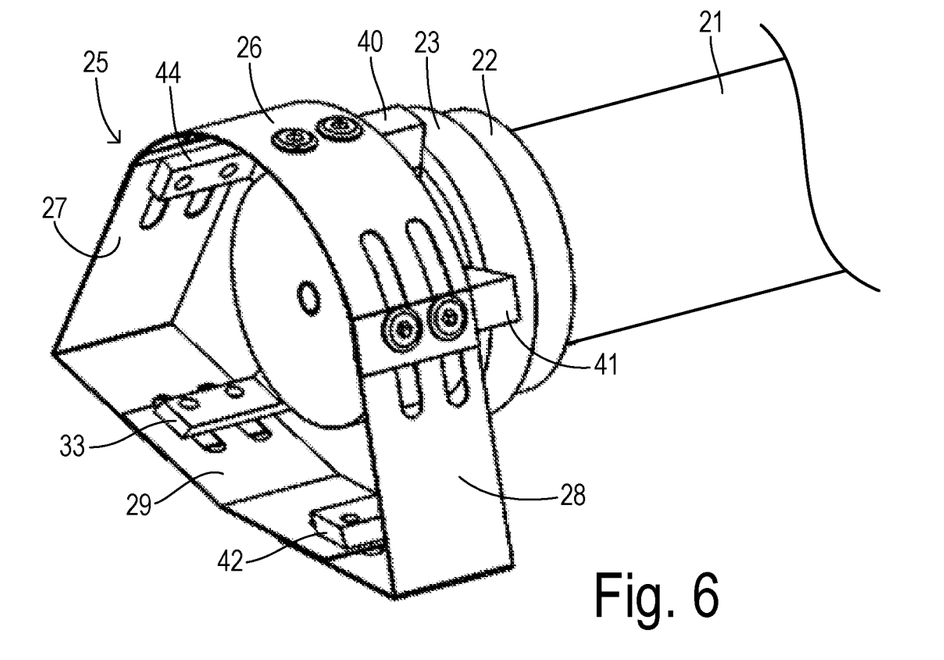
FIG. 6 is a perspective view of the cutting end of the tool of FIG. 3.
Figure 7:
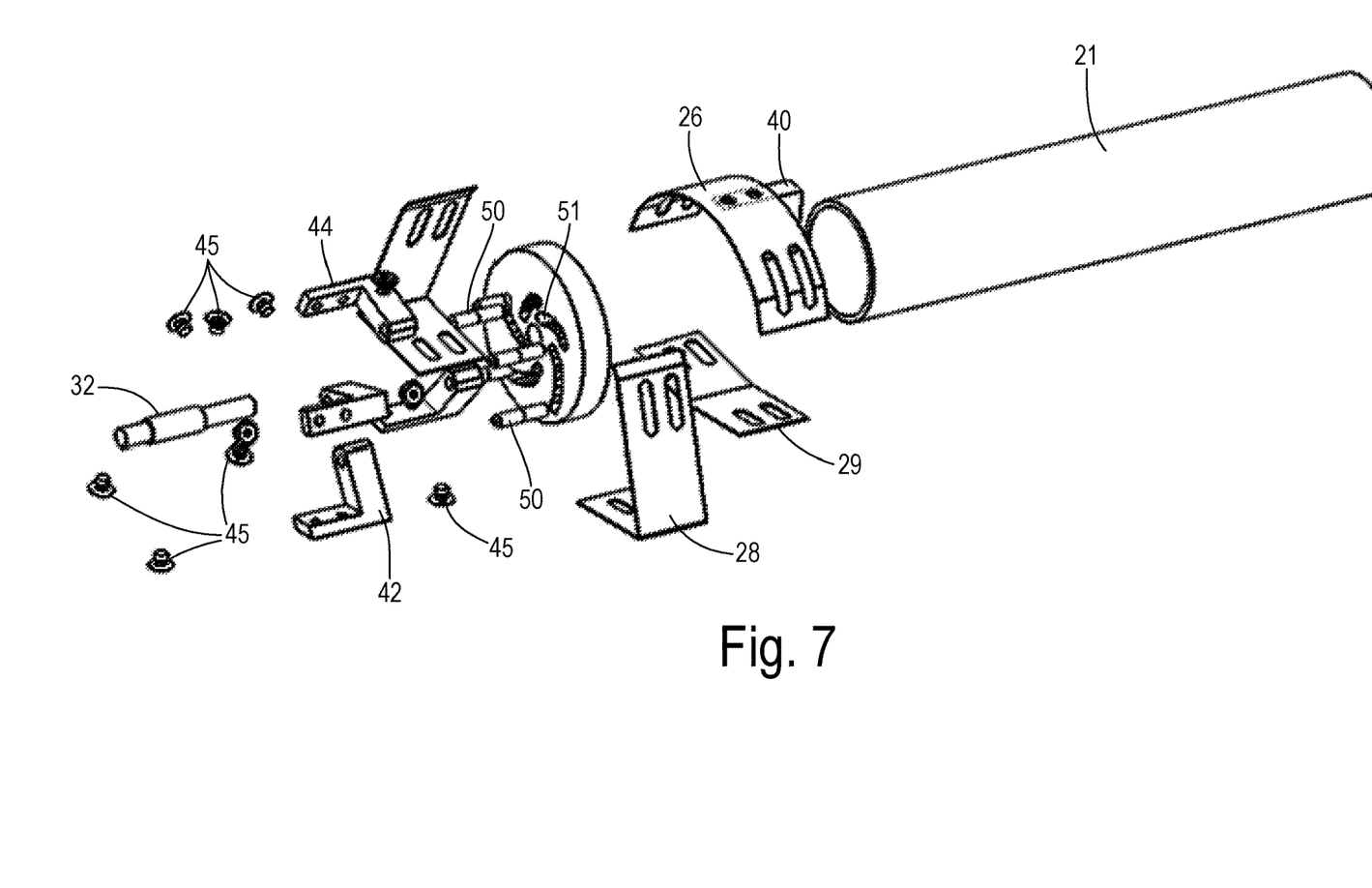
FIG. 7 is another partial exploded view of the tool of FIG. 3.
Figure 8:
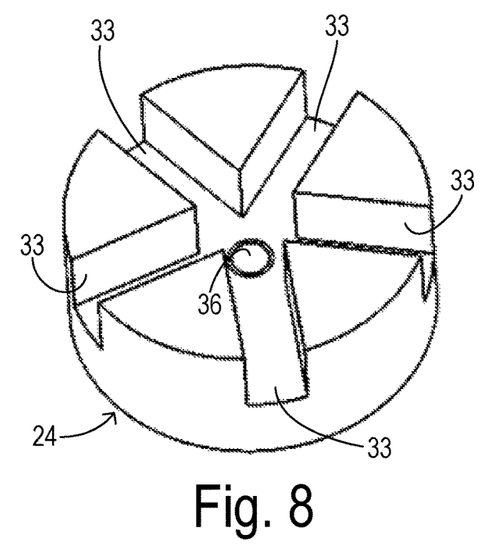
FIG. 8 is a perspective view of the cam block of FIG. 3.
Figure 9:
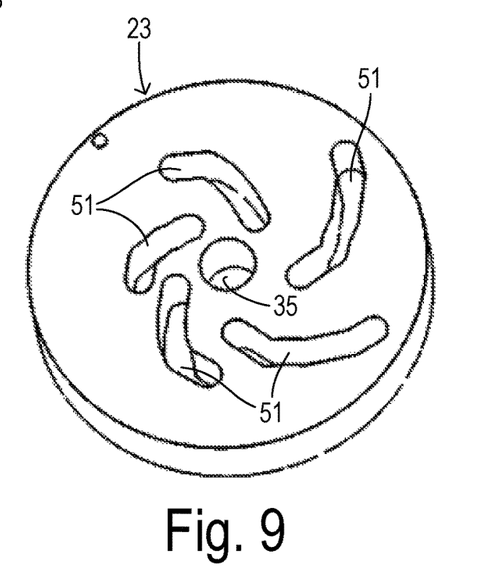
FIG. 9 is a perspective view of the adjustment wheel of FIG. 3.
Figure 10:
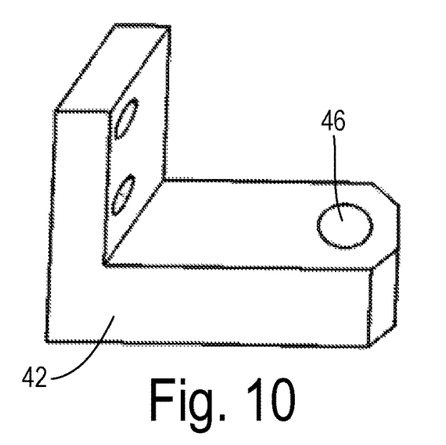
FIGS. 10 and 11 are perspective views of L-shaped links of FIG. 3.
Figure 11:
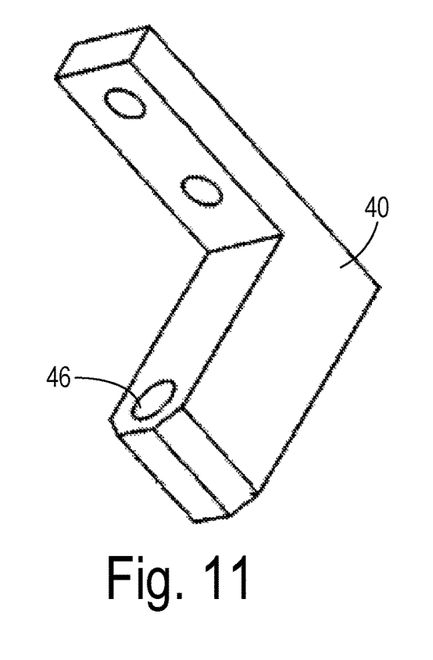
Figure 12:
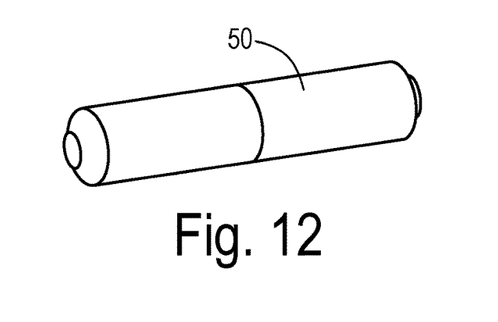
FIG. 12 is a perspective view of the guide pin of FIG. 3.
Figure 13:
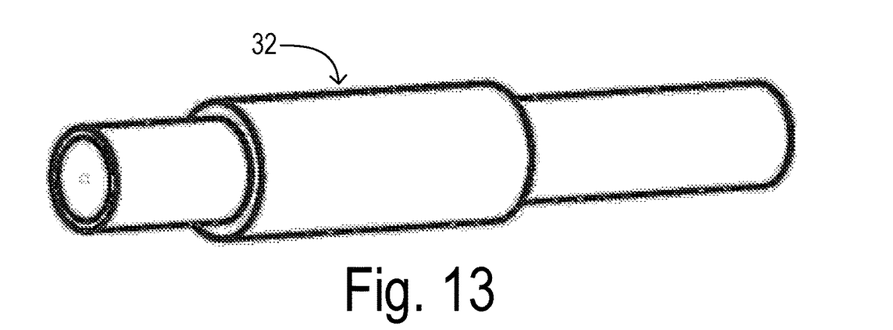
FIG. 13 is a perspective view of the shaft of FIG. 3.
Figure 14:
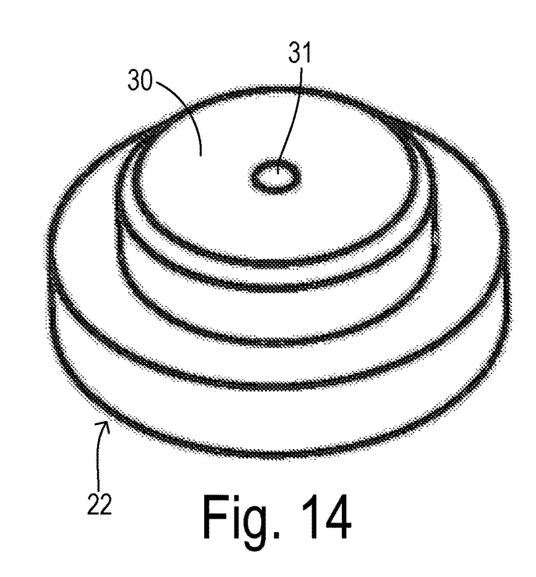
FIGS. 14 and 15 are perspective views of the base of FIG. 3.
Figure 15:
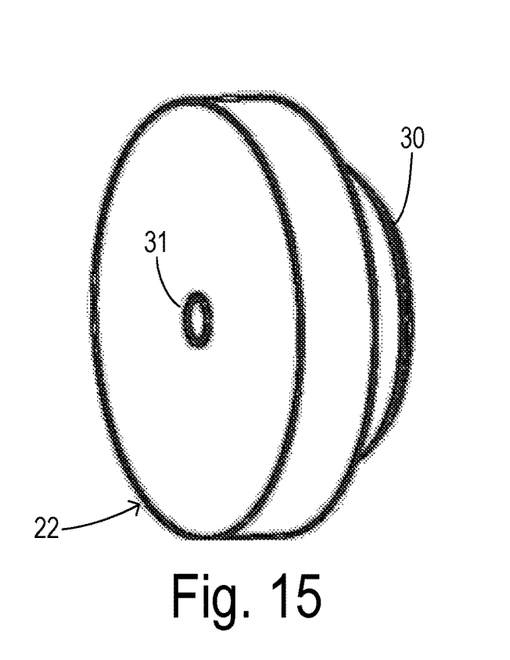
Figure 16:
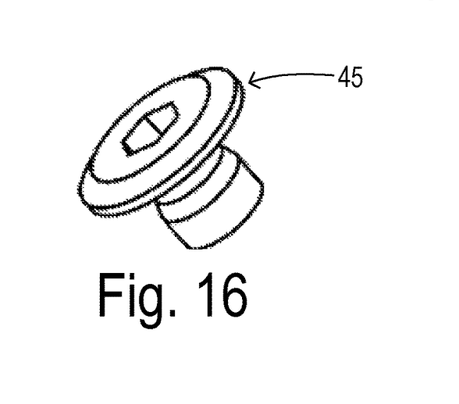
FIG. 16 is a perspective view showing a fastener in greater detail.

FIG. 6 is an end perspective view and FIG. 7 is a corresponding exploded view of tool 20. Base 22 and cam block 24 are removed from FIG. 7 for clarity. L-shaped links 40-44 are attached by a plurality of fasteners 45 to blade segments 26-29. Link 40 is non-movably attached to blade segment 26, while links 41-44 are slidable along respective slots in blade segments 27-29, which adjusts the size and profile of a leaflet that will be cut when pressing the blades into the pericardium/membrane layer. The second legs of links 40-44 are received in radial slots 33 of cam block 24 (FIG. 8). As links 40-44 slide radially inward and outward within slots 33, the corresponding size of the cutter area is adjusted.

The second leg of each link 40-44 has a mounting hole 46 for fixedly receiving a respective guide pin 50. Guide pins 50 project into respective guide slots 51 formed in adjustment wheel 23. Slots 51 are spiral shaped, so that as wheel 23 is rotated on shaft 32, links 40-44 are driven in a radial direction as pins 50 are deflected along slots 51. As links 40-44 move radially inward or outward, cutting blade segments 26-29 slide over one another to modify an outer circumference of the cutter shape. To permit the movement, fasteners 45 are retained in oblong slots in blade segments 26-29. A spacing between an outer surface of each L-shaped link and an inner surface of each fastener is sufficient to allow the cutting blade segments within the space to slide freely.

Figure 17:
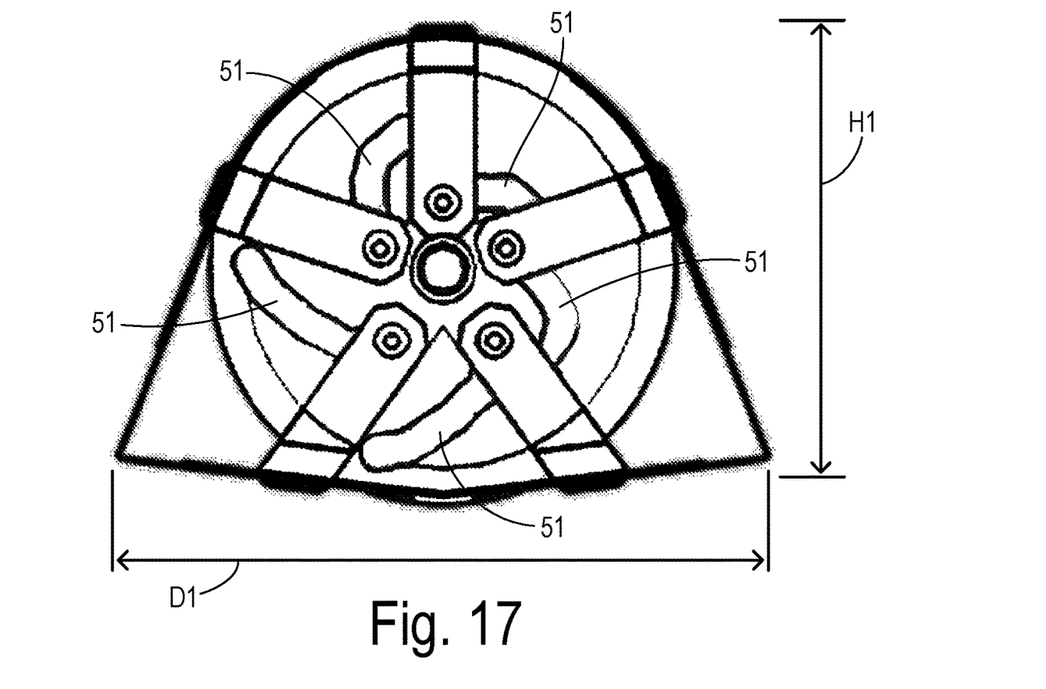
FIGS. 17 and 18 are end views showing the cutting tool adjusted to its smallest and largest leaflet sizes, respectively.
Figure 18:
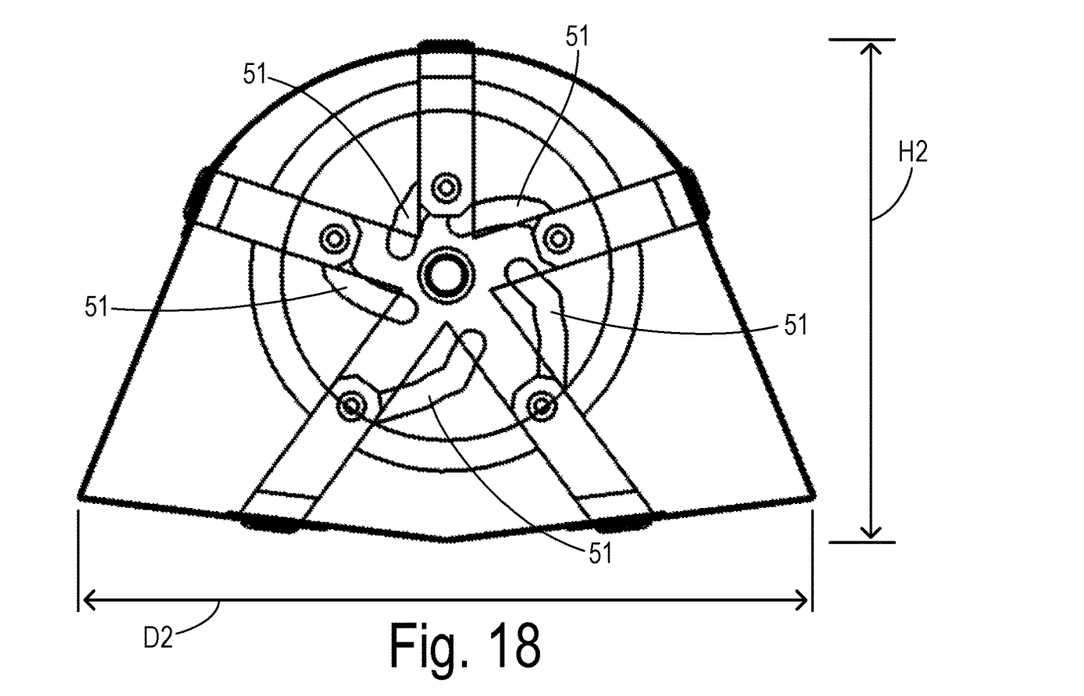
Figure 19:
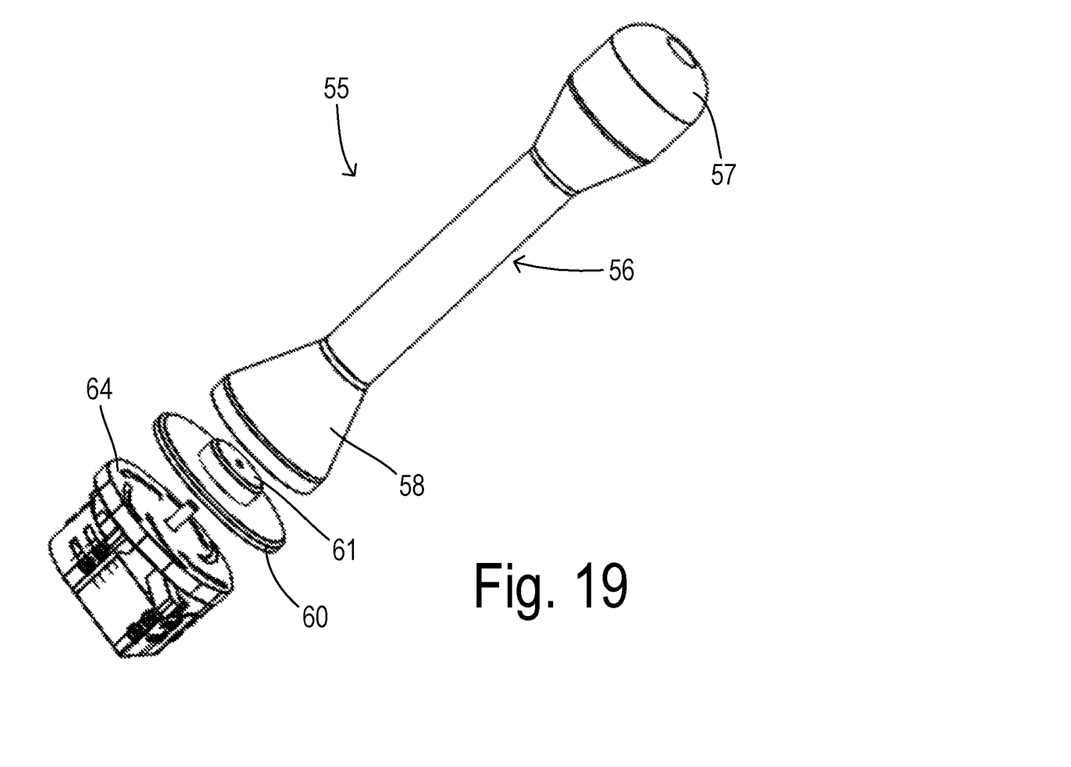
FIGS. 19-21 are exploded perspective views of a cutting tool according a second embodiment of the invention.
Figure 20:
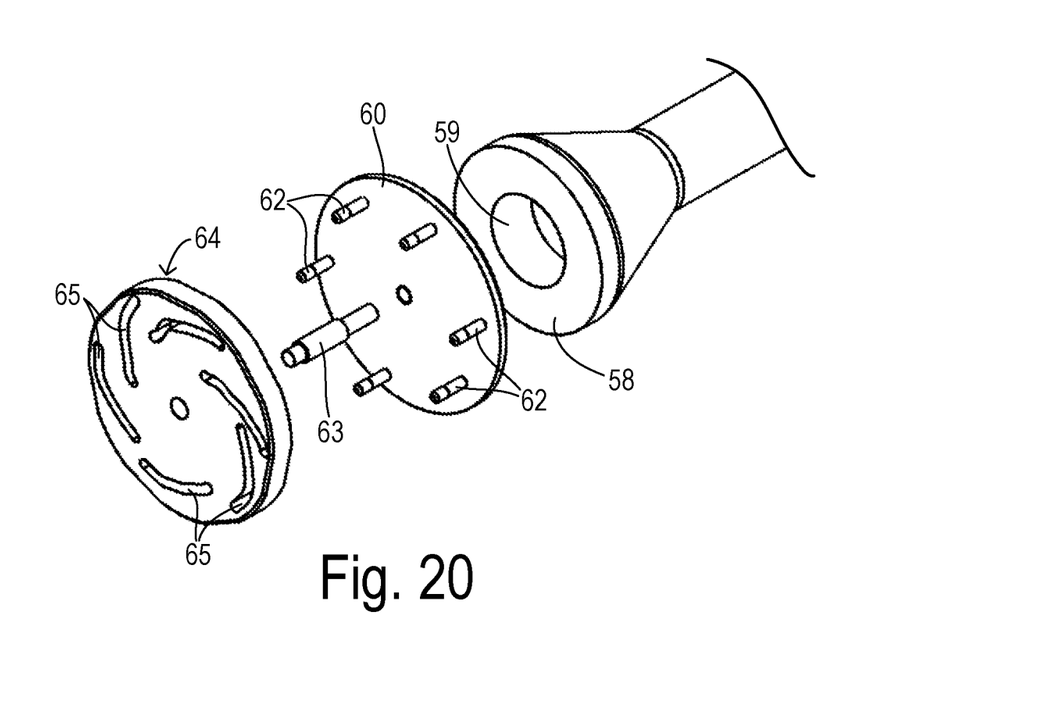
Figure 21:
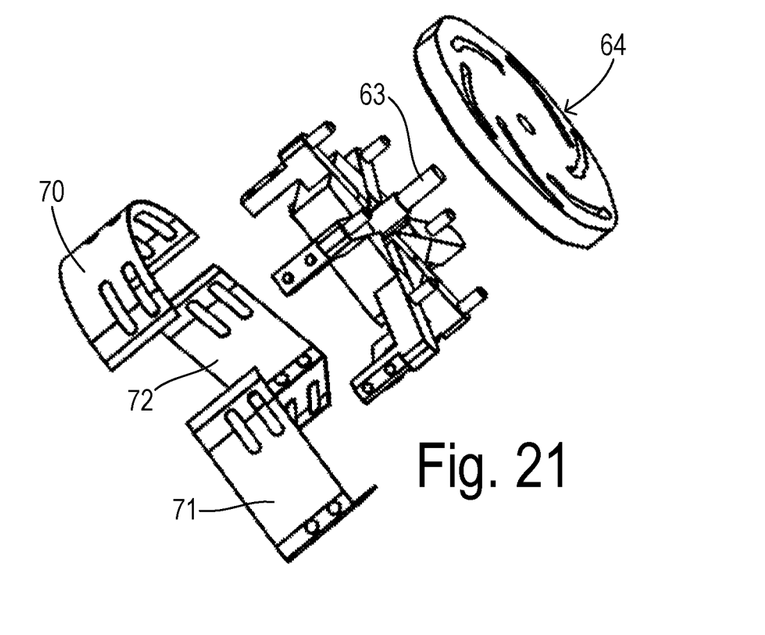
Figure 22:
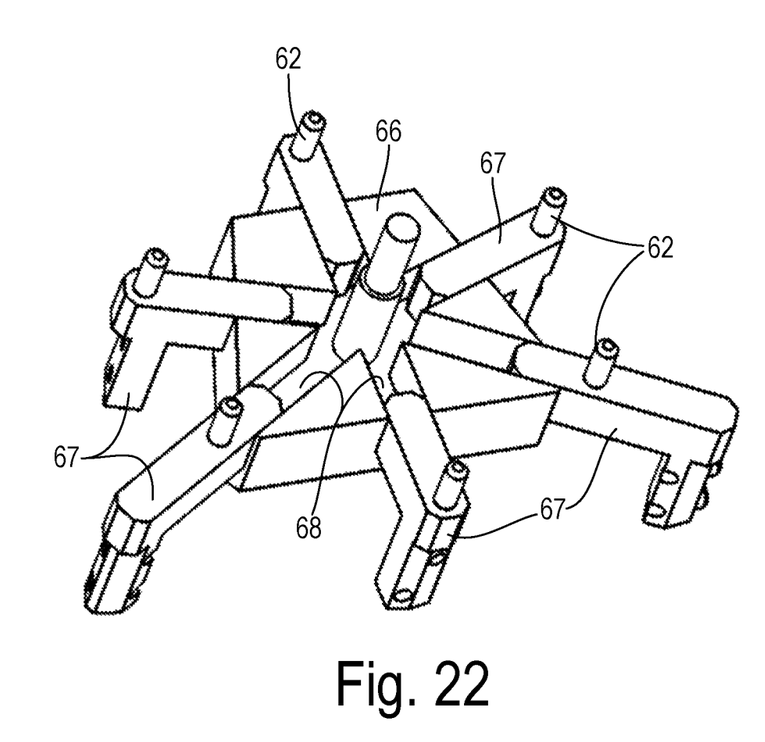
FIG. 22 is a perspective view of a cam block and links of the tool of FIG. 19.
Figure 23:
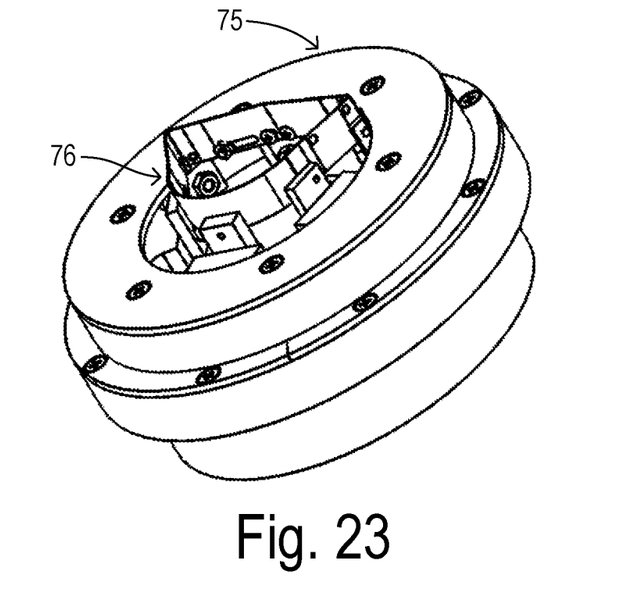
FIGS. 23 and 24 are bottom and side perspective views of a cutting tool according a third embodiment of the invention.
Figures 24, 28:
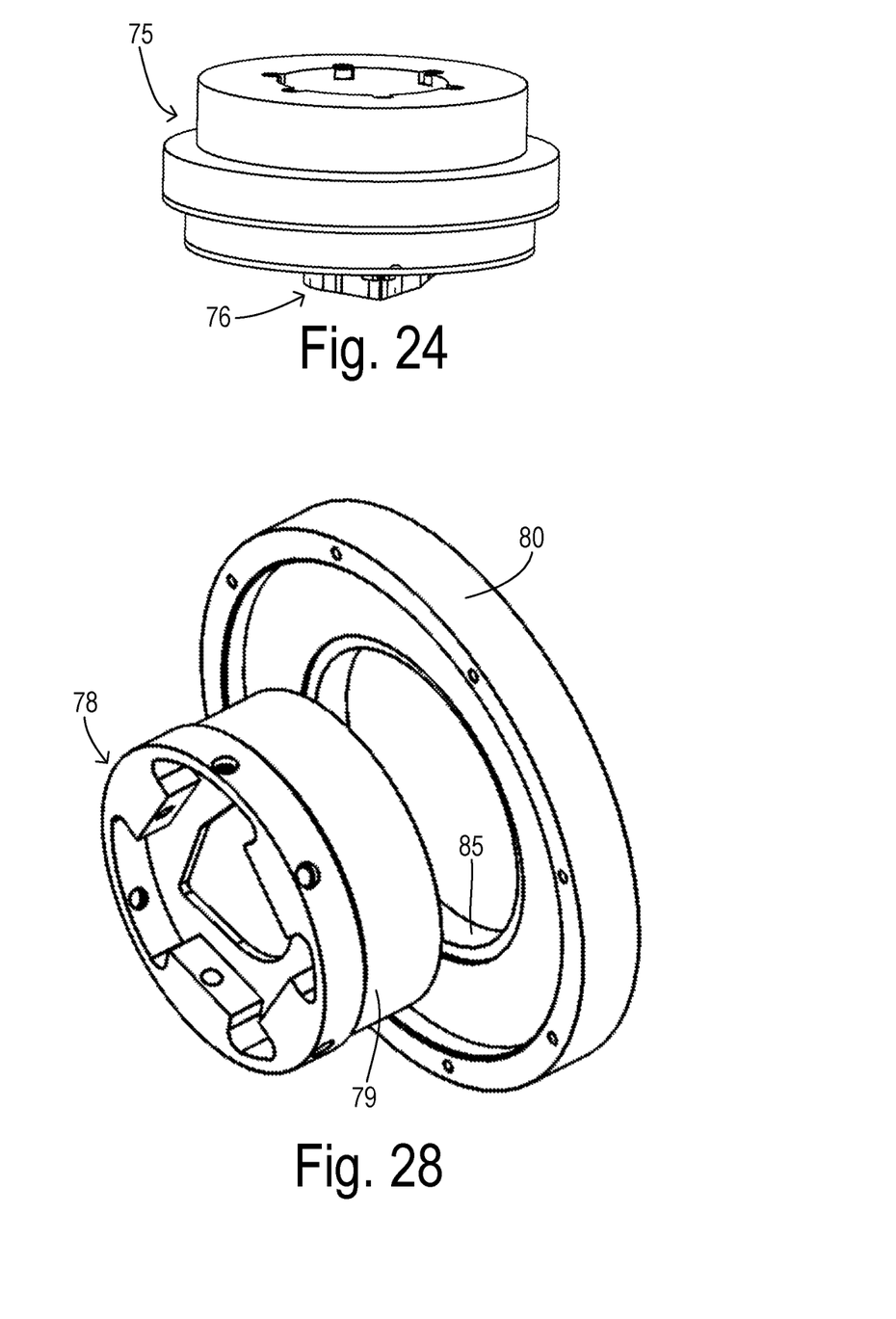
FIG. 28 show components providing an adjustment mechanism for the tool of FIG. 23.
Figure 25:
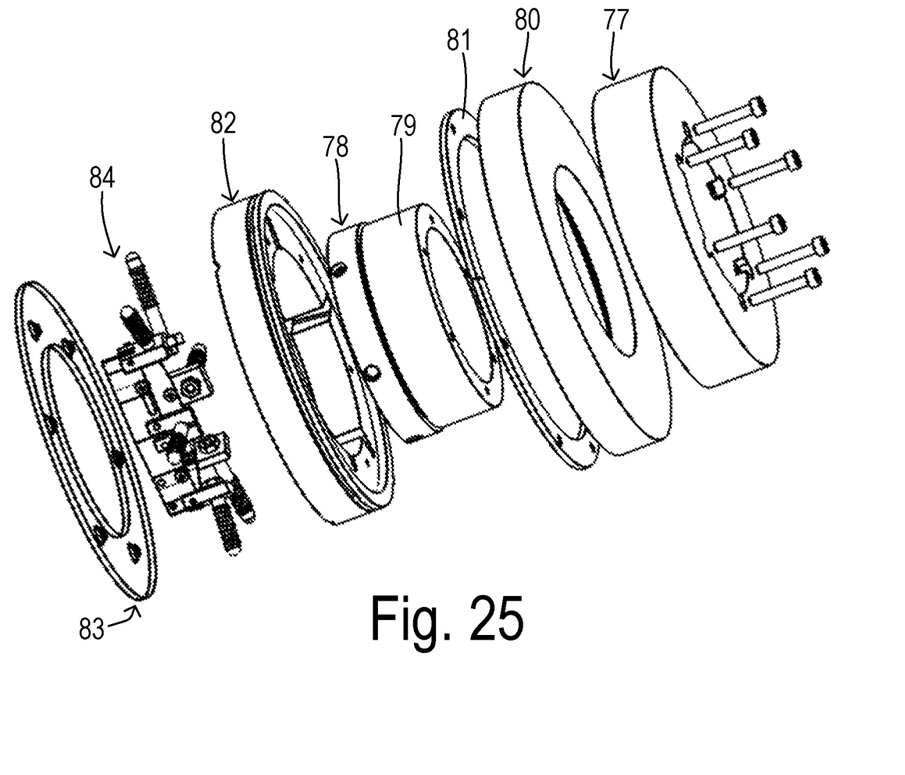
FIG. 25 is an exploded view of the cutting tool of FIG. 23.
Figure 26:
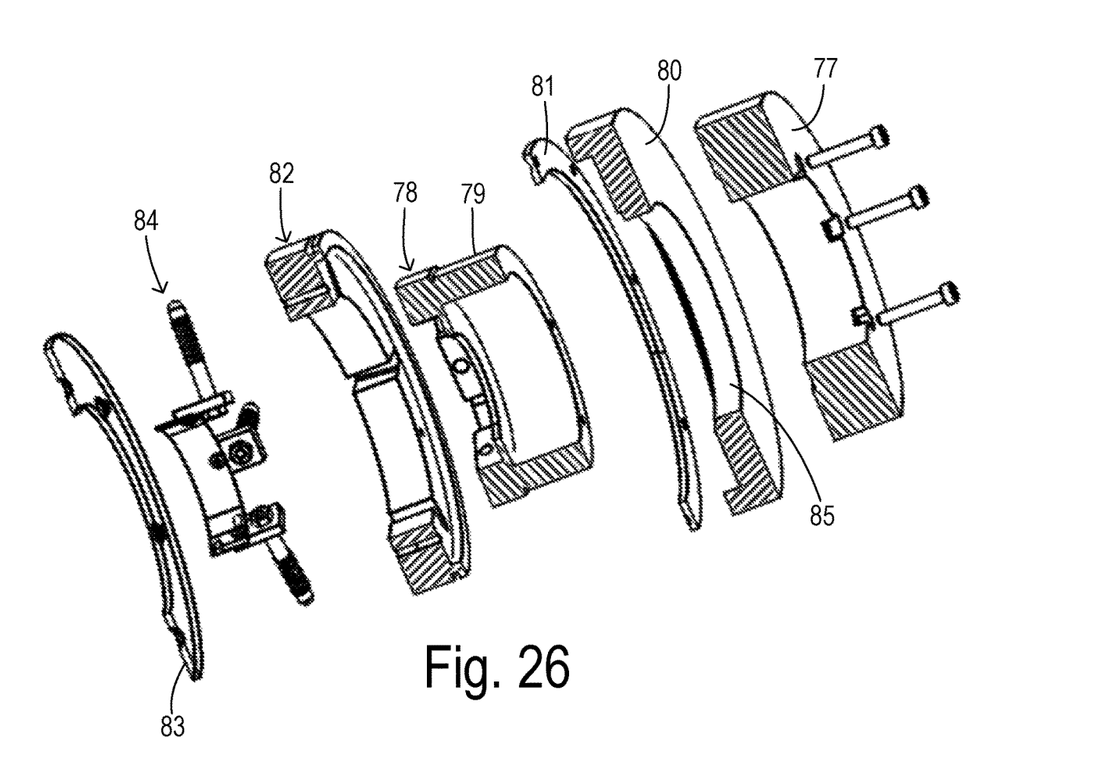
FIG. 26 is a cross-sectional exploded view of the tool of FIG. 25.
Figure 27:
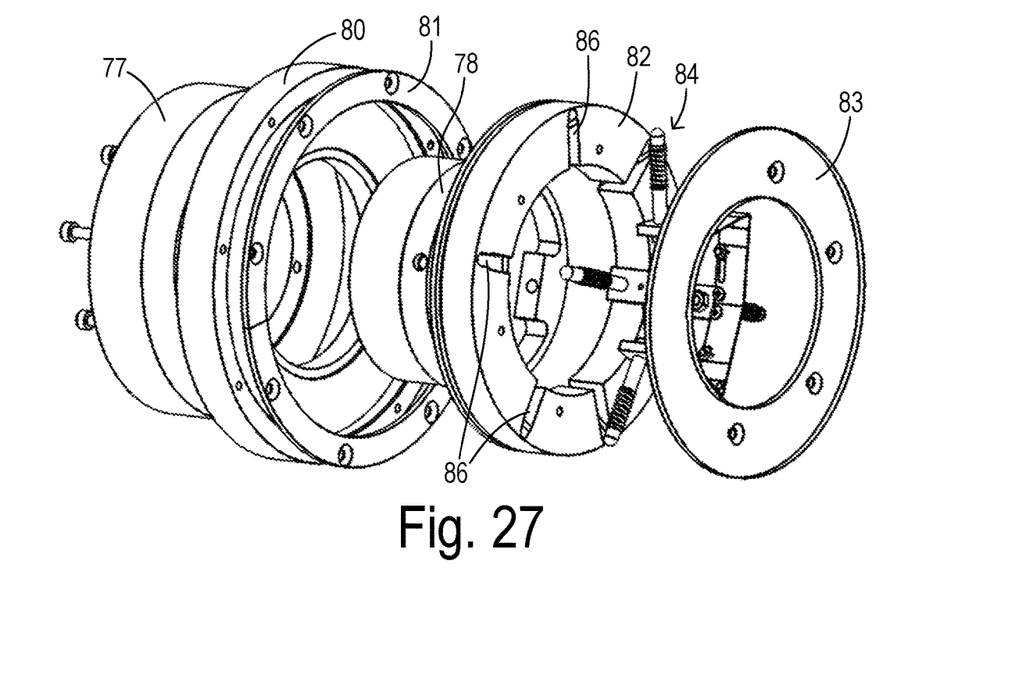
FIG. 27 is another exploded, perspective view of the tool of FIG. 23.

FIGS. 17 and 18 are end views showing the minimum and maximum sizes, respectively, for the cutter area. In FIG. 17, guide pins 50 are at the innermost ends of slots 51, so that a minimum leaflet diameter D1 and a minimum leaflet height H1 are obtained. By sufficiently rotating adjustment wheel 23, guide pins 50 slide along respective slots 51 to the opposite ends of the slots so that a maximum leaflet diameter D2 and a maximum leaflet height H2 are obtained. Adjustment wheel 23 can carry indicator markings (not shown) that are calibrated to inform the user of an effective width of a leaflet to be cut at corresponding positions of wheel 23.

FIGS. 19-22 illustrate a second embodiment wherein a cutting tool 55 has a contoured handle 56. Handle 56 has a narrow central shaft with a widened push-grip 57 at a proximal end and an expanding socket 58 at a distal end. Socket 58 has a center bore 59 for fixedly mounting a shank 61 of a base plate 60. Similar to the first embodiment, guide pins 62 ride in guide slots 65 of an adjustment wheel 64. A shaft 63 is fixed to plate 60 and rotatably retains adjustment wheel 64. Guide pins 62 are mounted to respective legs of L-shaped links 67 which are slidably retained in grooves 68 in a cam block 66. Radially inward and outward movement of links 67 under control of rotating adjustment wheel 64 is transferred to sliding cutter blade segments 70-72 to provide a desired profile to cut a leaflet having the desired dimensions.

FIGS. 23-30 illustrate a third embodiment of a cutting tool having a handle portion 75 and a cutting portion 76. Handle portion 75 includes a stationary end block 77 which is rigidly mounted to a spindle 78 by screws or other fasteners. Spindle 78 has a threaded outside surface 79 onto which an adjuster block 80 is threaded via internal threads 85. A slide plate 81 is mounted onto a peripheral edge of adjuster block 84 to press against and slide along one side of a push block 82. Push block 82 receives an end plate 83 for closing off a plurality of internal slots 86 in push block 82. Cutting portion 76 has a cutting blade arrangement 84 captured in slots 86.

Figure 29:
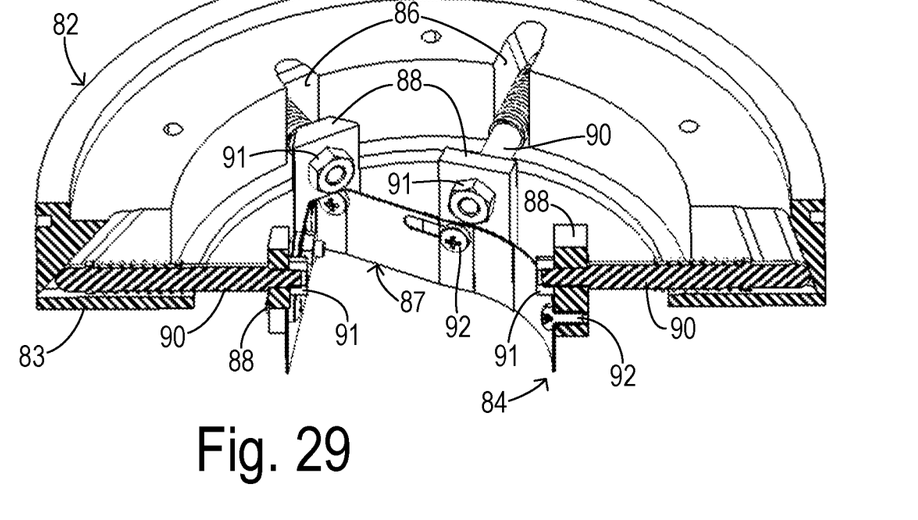
FIG. 29 is a cross-sectional view showing a mechanism for controlling a cutting size in response to manual adjustment.
Figure 30:
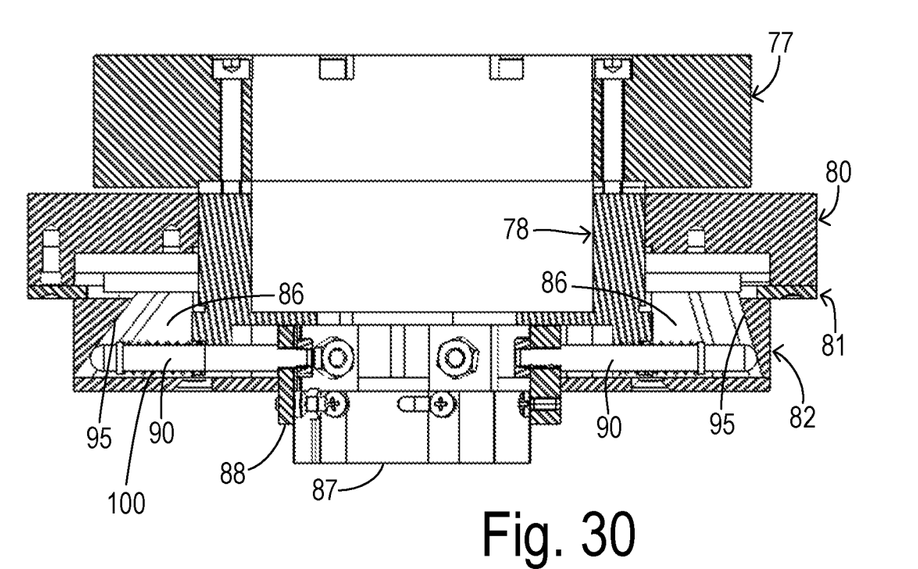
FIG. 30 is a cross section showing the adjustment mechanism in greater detail.

As best shown in FIGS. 29 and 30, a plurality of pins 90 support respective cutting blade segments 87 via support blocks 88. Each blade segment 87 has an elongated slot receiving a mounting screw 92 which fastens to a respective support block 88 with enough clearance to allow circumferential sliding of blade segments 87. One end of each pin 90 is mounted to a respective support block via an attachment nut 91. Thus, radial movement of pins 90 translates into changes in the size of the cutting profile of blade segments 87.

More specifically, pins 90 are thrust radially inward by downward axial movement of push block 82 (FIG. 30) which is obtained by rotating adjuster block 80 along the threaded surface of spindle 78. Downward movement of push block 82 places each pin 90 against a different region of a slotted end surface 95 of slots 86. Support blocks 86 are arranged to abut spindle 78 as seen in FIG. 30. Thus, with end block 77 and spindle 78 being held stationary, adjuster block 80 is rotated to move axially along threads 79 which pushes push block 82 axially to adjust the longitudinal positioning of pins 90 within slots 86. Preferably, each pin 90 may carry an outer spring 100 arranged to urge it radially outward to maintain contact against slanted surface 95 of each respective slot 86. Spring 100 is preferably captured between a raised flange on pin 90 and a barrier wall or niche of spindle 78.

What is claimed is:

1. A device for preparing leaflets for cardiovascular valve reconstruction, comprising:
   a plurality of blade segments forming a closed periphery for penetrating a membrane to cut a leaflet, wherein the blade segments are circumferentially slidable over one another;
   radially-slidable links slidably attached to respective blade segments; and
   an adjustment disc coupled to the links, wherein rotation of the adjustment disc varies a radial position of the links which modifies an overlapping of the blade segments, wherein the modifying of the overlapping of the blade segments allows selection of a corresponding size of the closed periphery.

2. The device of claim 1, wherein each blade segment includes an elongated slot receiving a fastener for slidably attaching the blade segment to the respective slidable link.

3. The device of claim 1, further comprising:
a cam block having radial slots receiving a respective link; and
guide pins fixed to respective links perpendicular to the radial slots;
wherein the adjustment disc has spiral guide slots each receiving a respective guide pin.

4. The device of claim 3, wherein each one of the slidable links is comprised of an L-shaped member with a radial leg received in a respective radial slot and an axial leg connected to a respective blade segment.

5. The device of claim 1, further comprising:
a spindle having a threaded outer surface; and
a push block having a plurality of internal channel-shaped slots with slanted end walls;
wherein the adjustment disc is comprised of a disc with a threaded, inner cylindrical surface engaging the threaded outer surface of the spindle;
wherein rotation of the disc causes axial movement of the disc which is transferred to the push block; and
wherein the links are comprised of pins coupled to the blade segments and disposed in the internal slots of the push block to engage the slanted end walls which converts the axial movement of the push block into radial movement of the pins.

6. The device of claim 5, further comprising an end plate mounted to an axial end of the push block for enclosing the pins in the internal slots.

* * * * *